United States Patent [19]

Cobb et al.

[11] Patent Number: 4,461,897
[45] Date of Patent: Jul. 24, 1984

[54] PROCESS FOR THE PRODUCTION OF SULFENAMIDES

[75] Inventors: Alec S. Cobb, Overijse, Belgium; David J. Williams, Salop, England

[73] Assignee: Monsanto Europe S.A., Brussels, Belgium

[21] Appl. No.: 423,428

[22] Filed: Sep. 24, 1982

Related U.S. Application Data

[63] Continuation of Ser. No. 209,179, Nov. 21, 1980, abandoned.

[30] Foreign Application Priority Data

Nov. 23, 1979 [GB] United Kingdom ................ 7940652

[51] Int. Cl.$^3$ ........................................... C07D 277/80
[52] U.S. Cl. ................................. 544/135; 204/59 R; 502/163; 548/167
[58] Field of Search ........................................ 548/167

[56] References Cited

U.S. PATENT DOCUMENTS

| | | | |
|---|---|---|---|
| 3,116,328 | 12/1963 | Cox et al. | 260/567 |
| 3,116,329 | 12/1963 | Hayes et al. | 260/567 |
| 3,600,398 | 8/1971 | Svarz et al. | 260/306.6 |
| 3,654,297 | 4/1972 | Goulandris | 260/306.5 |
| 3,737,431 | 6/1973 | Campbell et al. | 260/247.1 |
| 4,072,630 | 2/1978 | Douglas | 252/430 |
| 4,087,378 | 5/1978 | Carlson | 252/431 |
| 4,127,454 | 11/1978 | Torii et al. | 204/59 R |
| 4,258,197 | 3/1981 | Toukan | 548/167 |

FOREIGN PATENT DOCUMENTS 1407649 10/1972 United Kingdom .
1407917 11/1972 United Kingdom .

OTHER PUBLICATIONS

Journal of Molecular Catalysis, 5(1979), 109–123, "Autoxidation of Mercaptans Promoted by a Bifunctional Catalyst Prepared by Polymer Attachment of Cobalt-Phthalocyanine, J. H. Schutten and J. Zwart.

Primary Examiner—Donald G. Daus
Assistant Examiner—D. B. Springer
Attorney, Agent, or Firm—Gordon B. Seward

[57] ABSTRACT

Benzothiazole-2-sulfenamides are prepared by reacting a 2-mercaptobenzothiazole and a primary or secondary amine with oxygen in the presence of a catalyst, for example a metal phthalocyanine, in a reaction medium consisting of (i) a mixture of the amine and water in which the amount of water at the outset of the reaction is from 0.2 to 20% by weight of the mixture, or (ii) a mixture as defined in (i) diluted with an inert organic solvent miscible with the mixture, in a proportion of up to two parts by weight of the inert organic solvent per part by weight of the mixture.

7 Claims, No Drawings

PROCESS FOR THE PRODUCTION OF SULFENAMIDES

This is a continuation of application Ser. No. 209,179, filed Nov. 21, 1980, abandoned.

This invention relates to a process for the production of sulfenamides which are useful as accelerators in the vulcanization of rubber.

BACKGROUND OF THE INVENTION

Processes for the production of sulfenamides by the reaction of primary or secondary amines with mercaptans such as 2-mercaptobenzothiazole in the presence of oxygen and a metal phthalocyanine catalyst, are described in U.S. Pat. No. 3,737,431. According to that description, the reaction can be carried out in a reaction medium which is an aqueous medium, a mixed aqueous-organic medium, or an organic medium. Most of the detailed examples are of processes in which the reaction medium contains a major amount of water relative to the amount of the primary or secondary amine, and the only wholly organic reaction media disclosed employ pyridine as the organic solvent.

U.K. Patent Specification No. 1,407,649 describes a process in which a 2-mercaptobenzothiazole is condensed with ammonia or a primary or secondary amine in the presence of oxygen using copper or a copper compound other than a copper phthalocyanine as a catalyst. The reaction medium may be aqueous, organic or aqueous organic, and when the reactant that is condensed with the 2-mercaptobenzothiazole is an amine, an excess of the amine can be used as the solvent for the reaction.

SUMMARY OF THE INVENTION

We have now discovered that the yield of sulfenamide obtainable in this type of process can be maximized by using a reaction containing an excess of the primary or secondary amine and a small, controlled quantity of water.

The process of the invention for the production of a sulfenamide comprises reacting a 2-mercaptobenzothiazole of the formula

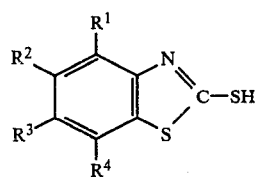

where each of $R^1$, $R^2$, $R^3$, and $R^4$ is independently hydrogen, $C_{1-6}$ alkyl, $C_{1-6}$ alkoxy, chloro- or other inert substituent and an amine which is a primary alkylamine or cycloalkylamine, or a secondary amine having the formula

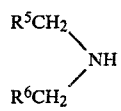

where each of $R^5$ and $R^6$ is hydrogen or an alkyl or cycloalkyl group or where $R^5$ and $R^6$ are linked such that the amine has a saturated ring structure optionally containing a hetero-atom in addition to the nitrogen atom shown in the formula, with oxygen in the presence of a catalyst in a reaction medium containing water and a stoichiometric excess of the amine relative to the 2-mercaptobenzothiazole, and is characterized in that the reaction medium consists of (i) a mixture of the amine and water in which the amount of water at the outset of the reaction is from 0.2 to 20% of the weight of the mixture, or (ii) a mixture as defined in (i) diluted with an inert organic solvent miscible with the mixture, in a proportion of up to two parts by weight of the inert organic solvent per part by weight of the mixture.

The above definition refers to the composition of the reaction medium at the outset of the reaction, because during the reaction the composition changes, substantially one mole of amine being consumed and one mole of water being produced per mole of sulfenamide formed. The 2-mercaptobenzothiazole reactant is not regarded as a component of the reaction medium.

DESCRIPTION OF THE PREFERRED EMBODIMENTS

If an inert organic solvent is employed, this must be such that it does not react with the 2-mercaptobenzothiazole in competition with the amine (so that primary or secondary amines other than the one used in the process are in general excluded), or otherwise have an adverse effect on the process. Preferred organic solvents are polar compounds, examples of which are alcohols, for example, methanol, ethanol and isopropanol, glycols, for example ethylene glycol, ketones, for example acetone and methyl isobutyl ketone, tertiary amines, for example triethylamine and pyridine, nitriles, for example acetonitrile, amides for example dimethylformamide, sulfones and sulfoxides for example dimethylsulfoxide. Usually, however, it is preferred not to use a diluent because its presence complicates the recovery of the excess amine and often the recovery of the sulfenamide product.

Within the range 0.2 to 20% by weight of water in the amine/water mixture, there is usually an optimum concentration of water corresponding to a maximum yield of product. This concentration may vary, depending on the particular amine, catalyst and other factors, for example the reaction temperature, but the lower limit of the range of water contents within which the optimum is found is normally not below 0.25% and often not below 0.5%, while the upper limit is usually not above 15% and often not above 10% or sometimes 5%. Thus, typical ranges within which the optimum water content may be found are 0.25 to 15%, 0.5 to 15%, 1 to 15%, 0.25 to 10%, 0.5 to 10%, 1 to 10%, 0.25 to 5%, and 0.5 to 5%, when all percentages refer to the percent by weight of water in the amine/water mixture. For instance, in the production of N-tert-butyl-2-benzothiazolesulfenamide using cobalt phthalocyanine catalysts, the optimum concentration of water in the tert-butylamine/water mixture is within the range 2 to 4% by weight.

While it is preferred to operate at the optimum water concentration, the present invention is not limited to such operation. In general, improved yields and/or product quality relative to those obtainable by prior art catalytic oxidation processes, are obtained using water concentrations within the ranges specified above.

The process is typically carried out at a temperature in the range 50° to 85° C. Reaction times at temperatures below about 50° C. tend to be impractically long, and there is a tendency for the yield of product to decrease due to over-oxidation at temperatures much above 70°-75° C. The optimum reaction temperature depends, inter alia, on the particular amine reactant, but is usually within the range 55° to 75° C., for example 60° to 65° C. or 65° to 75° C.

The oxygen required in the process can be introduced as such or in admixture with an inert diluent gas, for example as air. The reaction is preferably carried out in an autoclave at pressures at from 0.14 to 0.7 MPa gauge pressure, typical operating pressures being within the range 0.35 to 0.5 MPa when using oxygen, and within the range 0.4 to 0.6 MPa when using air. (Gauge pressure is 1 atmosphere (0.103 MPa) less than absolute pressure). The pressure can be maintained substantially constant by supplying oxygen continuously to replenish that consumed in the reaction, or the pressure in the autoclave can be allowed to vary between a maximum and a minimum. In the latter procedure, the pressure falls from the upper to the lower value as oxygen is consumed, and further oxygen is then supplied to the autoclave to restore the pressure to the upper value. This sequence is repeated until the pressure essentially ceases to fall, i.e. no more oxygen is being consumed, and the reaction is assumed to be complete. When the oxidation is carried out with air, it is desirable to release the nitrogen from the autoclave intermittently or continuously to avoid an overall increase in pressure as the reaction proceeds.

The reaction mixture should be stirred or otherwise agitated as efficiently as possible throughout the reaction.

As indicated previously, various materials, for example copper metal and a range of metal compounds, are known in the art as catalysts for the oxidative condensation of a 2-mercaptobenzothiazole with a primary or secondary amine using oxygen as the oxidizing agent.

Whereas U.S. Pat. No. 3,737,431 discloses only the use of metal phthalocyanines, we have found that related complexes are also effective catalysts, and the preferred catalysts for use in the process of the present invention are metal complexes of porphyrazine and its derivatives, particularly the class of complexes having the formula

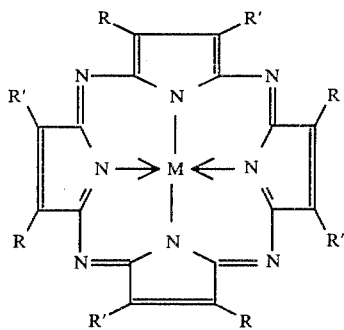

where M represents a metal atom, for example cobalt, manganese, vanadium, chromium, nickel, iron, copper or platinum, and each of R and R' represents hydrogen, alkyl, for example methyl or ethyl, halogen, for example chlorine, alkoxy, nitro or acetyl, or R and R' together represents an aromatic (including heteroaromatic) nucleus fused to the pyrrole ring. Examples of such aromatic nuclei are the nuclei of benzene, naphthalene, pyridine and quinoline which nuclei may themselves carry substituent atoms or groups, for example alkyl, such as methyl or ethyl, halogen, for instance chlorine or bromine, alkoxy, acetyl, nitro, alkylcarbonyl, carboxy, alkoxycarbonyl, hydroxysulfonyl or sulfenamide. The atoms or groups R and R' attached to different pyrrole rings in the porphyrazine structure may be the same or different Examples of porphyrazine derivatives useful as catalysts in the present invention are, (in addition to the metal phthalocyanines disclosed in U.S. Pat. No. 3,737,431), the cobalt and manganese complexes of porphyrazine itself, octamethylporphyrazine and derivatives where R and R' together represent

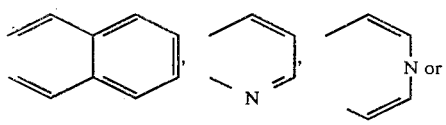

In the process of U.S. Pat. No. 3,737,431, when the reaction medium is aqueous or aqueous-organic, the phthalocyanine metal complexes employed in the process of U.S. Pat. No. 3,737,431 are water-soluble complexes, water solubility being conferred by the presence of sulfonic acid or other polar groups as substituents in the benzene nuclei of the phthalocyanine molecule. Some at least of the sulfonic groups may be present in the form of salts with the primary or secondary amine or with an alkali metal or alkaline earth metal. Such catalysts can be used in the present invention.

However, procedures for isolation of the sulfenamide from the final reaction mixture often involve mixing the latter with water, and a disadvantage of water-soluble catalysts is that separation of the catalyst from the reaction mixture for recycling and reuse is not straightforward. A catalyst insoluble in the reaction medium which can be separated by filtration is therefore advantageous. We have found that the use of catalytic material in which the active catalyst is adsorbed on a water-insoluble solid adsorbent support can be used with very good results in the process of the present invention. The active catalyst that is supported in such materials is preferably one that is substantially water-insoluble, for example metal complexes of unsubstituted phthalocyanine or of phthalocyanines containing not more than one polar nuclear substituent, for instance phthalocyanine monosulfonic acid.

The most active supported catalysts are generally those having cobalt or manganese complexed with phthalocyanine or with tetrapyridine porphyrazine, but chromium, nickel, copper, platinum, vanadium and iron complexes with phthalocyanine can be used. Vanadium and iron are preferably complexed with phthalocyanine monosulfonic acid when used in supported form.

Copper compounds are catalysts in the process of the invention, including copper phthalocyanine, and others as disclosed in British Specification No. 1,407,649. However, a disadvantage of most such compounds is that in addition to catalyzing the condensation of the mercaptobenzothiazole with the amine, they also appear to catalyze the further oxidation of the benzothiazolesulfenamide produced by the condensation. This leads to the production of by-products and lower yields and quality in the desired product.

Adsorbent solids which are suitable as catalyst supports for use in the process of the present invention include charcoals produced by the destructive distillation of wood, peat, coal, nut shells, bones or other carbonaceous matter, and preferably such charcoals as have been heat treated, or chemically treated, or both, to form a highly porous particle structure of increased adsorbent capacity, such charcoals being generally defined as activated carbon. The adsorbent solids also include naturally occurring clays and silicates, for example, diatomaceous earth, fuller's earth, kieselguhr, attapulgus clay, feldspar, montmorillonite, halloysite, and kaolin, and also the naturally occurring or synthetically prepared refractory metal oxides such as alumina or silica. In any case, a solid adsorbent material which has been activated by heat treatment, chemical treatment, or otherwise, to realize optimum porosity and adsorbent capacity is preferred.

Particularly good results have been obtained using an activated carbon obtained by the destructive distillation of coconut shells and acid washed to give a product having a surface area of 1300–1500 m²/g. and a bulk density of 0.40–0.44 g/ml. The particle size of the adsorbent solid support is not too critical, but supports having a particle size within the range 0.5 to 2 mm. have been found convenient to use in the practice. The amount of the catalyst adsorbed on to the support can vary, for example from 1% to 10% of the total weight of the support plus catalyst, amounts of from 2% to 6% being preferred. When such supported catalysts are used for the first time, up to 10% of the sulfenamide product is retained by adsorption on the support. This amount does not increase when the supported catalyst is recovered and reused.

In certain instances, the catalyst may be adsorbed on an anion exchange resin or, where the catalyst is a metal compound containing functional groups, it may be chemically coupled to a polymeric resin support containing groups reactive with those functional groups. Such resin carriers are, however, generally less satisfactory than the adsorbent solids referred to above.

The amount of catalyst employed in the process of the present invention can be, for example, from 0.1 to 2% relative to the weight of 2-mercaptobenzothiazole, and is preferably from 0.3 to 1.2% on the same basis.

The process of the invention is a catalyzed oxidative condensation of a 2-mercaptobenzothiazole and an amine. It is probable that the amine salt of the 2-mercaptobenzothiazole is an intermediate, and in any case, the 2-mercaptobenzothiazole can, if desired, be introduced into the reaction system as the preformed amine salt. Alternatively, the 2-mercaptobenzothiazole can be introduced into the reaction system in the form of the corresponding 2,2-bis(benzothiazolyl)disulfide, which is known to react with amines to form one molecule of sulfenamide (which is the required product of the process of the invention) and one molecule of the amine salt of the 2-mercaptobenzothiazole per molecule of the disulfide.

Primary alkylamines which can be used in the process of the invention include those where the alkyl group contains, for example, from 2 to 12 carbon atoms and has either a straight or branched chain, for example ethylamine, isopropylamine, tert-butylamine, sec-amylamine and tert-octylamine. The cycloalkyl group of a primary cycloalkylamine suitable for use in the process is usually one having five or six ring carbon atoms and optionally one or two alkyl, for instance methyl or ethyl, substituents, for example cyclopentylamine, cyclohexylamine and 2-methylcyclohexylamine. In secondary amines of the formula

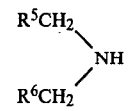

where $R^5$ or $R^6$ is an alkyl group, this can be, for example, an alkyl group having from 1 to 11 carbon atoms and having either a straight or branched chain. Where $R^5$ or $R^6$ is a cycloalkyl group, this will usually be one having five or six ring carbon atoms and optionally one or two alkyl, for instance methyl or ethyl, substituents. Examples of such secondary amines are dimethylamine, diethylamine, diisobutylamine, and cyclohexylmethyl methyl amine. Saturated heterocyclic amines which can be used in the process of the invention are generally compounds containing from 5 to 8 ring atoms including the nitrogen atom of the NH group, optionally another hetero-atom, for example oxygen or sulfur, and optionally one or two methyl or ethyl substituents. Examples of such amines are pyrrolidine, piperidine, 2-methyl-5-ethylpiperidine, morpholine, 2,6-dimethylmorpholine and hexamethyleneimine.

The preferred 2-mercaptobenzothiazole for use in the present process is 2-mercaptobenzothiazole itself where each of $R^1$, $R^2$, $R^3$, and $R^4$ is hydrogen. In preferred substituted 2-mercaptobenzothiazoles, two or three of $R^1$, $R^2$, $R^3$, and $R^4$ are hydrogen, and the other(s) is/are methyl or ethyl.

In the present process, the amount of the primary or secondary amine used is always in excess of the amount required as a reactant in the process. Normally at least 1.2 moles, and preferably at least 1.5 moles of amine, are used per mole of the 2-mercaptobenzothiazole. For example, the amount of amine may be from 1.5 or 2, to 20 moles per mole of 2-mercaptobenzothiazole. On mixing the amine and the 2-mercaptobenzothiazole, a salt is formed which, in many instances, has a limited solubility in the reaction medium. As a practical matter, therefore, the minimum excess in such cases may be set by the amount required to provide a stirrable reaction mixture at the reaction temperature. This amount will of course depend on the reaction temperature and on the equipment used. It may be desirable, moreover, to use more than the minimum excess, because a small increase in yield is observed as the excess is increased. It is usually preferred to use from 5 to 10 moles of amine per mole of 2-mercaptobenzothiazole.

The sulfenamide product is generally soluble in the reaction medium. Various methods can be employed for its isolation and for the recovery of the excess amine. A preferred method is to mix the reaction medium (after filtration if necessary to remove insoluble catalyst and catalyst support) with water, whereupon the sulfenamide is precipitated. Where the sulfenamide is a solid, it can be isolated by filtration of the slurry, and the excess amine can then be recovered from the filtrate. If desired, part of the excess amine can be distilled from the reaction mixture before dilution of the latter with water.

The invention is illustrated by the following Examples.

EXAMPLE 1

This Example describes the preparation of N-tert-butyl-2-benzothiazolesulfenamide.

222.7 Grams (3.05 moles) of tert-butylamine, 6.0 grams of water and 20 grams of a supported catalyst consisting of granules of activated carbon having a particle size 0.85–1.67 mm and a surface area 1300–1500 m$^2$/gram having adsorbed thereon 4% by weight of cobalt phthalocyanine and 8.5 grams of N-tert-butyl-2-benzothiazolesulfenamide from a previous preparation, were placed in an autoclave having a capacity of one liter. To this mixture, 66.8 grams (0.4 mole) of 2-mercaptobenzothiazole were added with stirring. The autoclave was then assembled and purged of air by pressurizing to 0.414 MPa gauge pressure with oxygen and releasing the pressure. After heating to 60° C., oxygen was added until a gauge pressure of 0.414 MPa was recorded. The pressure fell as oxygen was consumed in the reaction, and additional oxygen was added every 5 minutes to restore the pressure to 0.414 MPa. After 10–15 minutes, the source of heat was removed, the heat generated by the reaction being sufficient to maintain a temperature of 60°–65° C. After about 60 minutes, the oxygen pressure drop during 5 minutes fell by around 0.014 MPa, and at this stage the reaction was judged complete. The autoclave was then cooled to 30°–35° C. before releasing the pressure. The reaction mixture was stirred throughout the oxidation.

The contents of the autoclave were then filtered, the filtrate being essentially a solution of N-tert-butyl-2-benzothiazolesulfenamide in tert-butylamine. This solution was then added with stirring to 1500 mls of cold water, thereby precipitating the sulfenamide. The slurry was stirred and cooled to 20°–25° C. before filtering off the sulfenamide and washing with cold and hot water. After drying overnight at 50° C., 91.1 g (96% yield) of the sulfenamide (98.0% assay) were obtained.

This compares with the highest yield of N-tert-butyl-2-benzothiazolesulfenamide (80.5% based on 2-mercaptobenzothiazole) reported for a preparation using recycled catalyst in U.S. Pat. No. 3,737,431.

EXAMPLE 2

This Example illustrates the dependence of the yield of N-tert-butyl-2-benzothiazolesulfenamide on the amount of water initially present in the reaction medium, and on the molar ratio of tert-butylamine to 2-mercaptobenzothiazole.

The procedure was essentially that described in Example 1, but using varying quantities of amine and water as shown in the table below. In the table headings, TBS is tert-butylamine and MBT is 2-mercaptobenzothiazole.

| Preparation No. | Amount of Water grams | %* | Amount of TBA grams | moles | Product Yield on MBT % |
|---|---|---|---|---|---|
| 2A | 8.0 | 2.6 | 300 | 4.11 | 99.1 |
| 2B | 18.0 | 5.7 | 300 | 4.11 | 95.2 |
| 2C | 26.5 | 8.1 | 300 | 4.11 | 94.9 |
| 2D | 6.0 | 2.6 | 223 | 3.06 | 98.8 |
| 2E | 13.0 | 5.7 | 218 | 2.99 | 94.8 |
| 2F | 19.0 | 8.1 | 214 | 2.94 | 94.3 |
| 2G | 16.0 | 8.1 | 180 | 2.47 | 93.5 |
| 2H | 0.7 | 0.3 | 223 | 3.06 | 97.8 |

*Amount expressed as a percentage of the total weight of tert-butylamine and water in the initial reaction medium.

These results demonstrate that the yield of product is at a maximum when the amine/water mixture contains about 2.6% of water. On reducing the amount of water to 0.3% of the combined weight of the amine and water, the yield falls slightly below the maximum, but the most significant difference is that the reaction time, under the conditions of temperature and pressure indicated above in Example 1, is extended from the typical 60 minute period reported in Example 1 to 220–230 minutes.

As would be expected, reaction times are shortened by operating at higher reaction temperatures and/or pressures and by improving the efficiency of agitation of the reaction mixture. For example, as stated above, operation at 60°–65° C. with an initial water content of 0.3% by weight of the amine/water mixture requires a reaction time of 220–230 minutes, whereas this period can be reduced to 60 minutes by operating at about 70° C., an oxygen pressure of 0.518 MPa guage and a 25% increase in stirrer speed. The yield obtained is, however, less than that obtainable at an initial water content of 2.6% and otherwise identical reaction conditions.

EXAMPLE 3

In a number of preparations of N-tert-butyl-2-benzothiazolesulfenamide similar to those of Example 2 but using an unsupported soluble salt of polysulfonated cobalt phthalocyanine as the catalyst and between 6 and 7.5 moles of amine per mole of MBT, a similar effect was observed, i.e. the maximum yield was obtained in a tertiary butylamine/water reaction medium containing 97–98% by weight of the amine. Details are given in the table below.

| Preparation No. | %* Water | Product Yield on MBT % | Assay % |
|---|---|---|---|
| 3A | 16.0 | 89.2 | 95.5 |
| 3B | 8.5 | 91.8 | 97.5 |
| 3C | 5.4 | 96.3 | 97.1 |
| 3D | 2.6 | 97.7 | 97.9 |
| 3E | 1.3 | 96.5 | 98.0 |

*Amount of water as a percentage of the total weight of TBA plus water in the initial reaction medium

EXAMPLE 4

This Example describes the preparation of N-tert-butyl-2-benzothiazolesulfenamide using air as the oxidant.

The quantities of reactants were the same as in Example 1. The autoclave was modified to permit the continued bleed-off of nitrogen and excess oxygen while maintaining a gauge pressure of 0.414 MPa. The yield of N-tert-butyl-2-benzothiazolesulfenamide was 91.0 g (95.4%).

EXAMPLE 5

This Example describes the preparation of N-cyclohexyl-2-benzothiazolesulfenamide.

The procedure was essentially similar to that described in Example 1, using 205 grams (2.07 moles) of cyclohexyl-amine, 10.8 grams of water and 20 grams of supported catalyst containing 4% by weight of cobalt phthalocyanine. When the reaction was complete, the reaction mixture was filtered and the filtrate was poured into 3 liters of cold water thereby precipitating N-cyclohexyl-2-benzothiazolesulfenamide. The amount recovered after filtering, washing and drying, was 80.1 grams (77% yield on 2-mercaptobenzothiazole).

EXAMPLE 6

This example describes the preparation of 2(4-morpholinothio)benzothiazole.

Using the apparatus described in Example 1, oxygen was supplied to a stirred reaction mixture consisting of 237.5 g (2.73 moles) of morpholine, 12.5 g of water, 0.8 g of cobalt phthalocyanine polysulfonated catalyst supported on 20 g of activated carbon, and 66.5 g (0.2 moles) of 2,2-bis(benzothiazolyl)disulfide. The pressure was controlled as in Example 1 and the reaction temperature was 61°–65° C. After cooling at the end of the reaction to 50° C. and filtering to remove the catalyst, the filtrate was quenched with 2.7 liters of cold water. The slurry thus formed was filtered, and the solid retained on the filter was washed with water before drying at 50° C. 84.7 g (84%) of 2(morpholinothio)benzothiazole of 94.4% assay were obtained.

EXAMPLE 7

This Example describes the preparation of N-isopropyl-2-benzothiazole sulfenamide.

In the same apparatus as in Example 1, 400 g (6.77 moles) of isopropylamine, 10.0 g of water, 0.8 g of cobalt phthalocyanine supported on 20 g of activated carbon and 66.8 g (0.4 moles) of 2-mercaptobenzothiazole were oxidized by gaseous oxygen at a pressure of 0.414 MPa at 60°–66° C. On completion of the reaction, the catalyst was removed by filtration and the sulfenamide recovered by quenching the filtrate in 3.35 liters of cold water. After filtering, washing, and drying overnight at 50° C., 81.7 g (91.2%) of the sulfenamide were obtained at an assay of 98.1%.

EXAMPLE 8

This Example describes the preparation of N-tert-butyl-2-benzothiazolesulfenamide in a reaction medium containing an inert diluent.

87.7 Grams (1.2 moles) of tert-butylamine, 1.0 gram of water, 157 grams of isopropanol, 0.8 gram of cobalt phthalocyanine supported on 20 grams of activated carbon (also having adsorbed thereon 8.5 grams of N-tert-butyl-2-benzothiazolesulfenamide from a previous preparation) and 66.8 grams (0.4 mole) of 2-mercaptobenzothiazole were placed in an autoclave of 1 liter capacity. Oxygen was introduced into the autoclave and the stirred reaction mixture was oxidized following the procedure described in Example 1 except that the reaction temperature was maintained in the range 67°–71° C. On completion, the catalyst was recovered by filtration, and the sulfenamide was isolated by quenching the first filtrate in water and filtering the slurry thus obtained. The yield of N-tert-butyl-2-benzothiazolesulfenamide after washing and drying was 92%.

In similar experiments using 0.8 moles of tert-butylamine and 0.6 mole of tert-butylamine, with proportional reductions in the amounts of water and isopropanol, yields of N-tert-butyl-2-benzothiazolesulfenamide of 90.8% and 91.5% respectively were obtained. However, reducing the amount of amine to 0.48 mole (i.e. 1.2 moles per mole of 2-mercaptobenzothiazole and outside the scope of the present invention) also with proportional reductions in water and isopropanol, resulted in a fall in yield to about 80%.

EXAMPLE 9

This example describes the preparation of N-tert-butyl-2-benzothiazolesulfenamide using various metal phthalocyanines.

The quantities of reactants and the procedure were essentially those described in Example 1, but the metal phthalocyanine used varied as shown in the table below. Variations in reaction time and the yield of product are also given.

| Phthalocyanine Type | % Yield | Reaction Time (mins.) |
|---|---|---|
| Nickel | 77.4 | 170 |
| Iron | 74.2 | 130 |
| Platinum | 79.1 | 190 |
| Manganese | 88.8 | 75 |
| Chromium | 92.7 | 170 |
| Vanadium | 96.9 | 300 |
| Copper | 83.5 | 160 |

EXAMPLE 10

A series of experiments similar to those of Example 2 was carried out using a catalyst of manganese phthalocyanine supported on activated carbon. 0.4 Mole of 2-mercaptobenzothiazole and 2.6 moles of tert-butylamine. The reaction temperature was maintained in the range 60°–68° C. Variation of yield with the percent by weight of water in the amine/water reaction medium is shown in the table below.

| Preparation No. | % Water | % Yield of Product |
|---|---|---|
| 10A | 2.6 | 88.8 |
| 10B | 9.5 | 92.2 |
| 10C | 17.9 | 84.3 |
| 10D | 25.0 | 82.5 |
| 10E | 33.6 | 72.0 |

The results show the existence of a maximum in the yield of N-tert-butyl-2-benzothiazolesulfenamide. This may lie at 9.5% by weight of water in the amine/water reaction medium or possibly between 2.6% and 9.5%.

EXAMPLE 11

N-tert-butyl-2-benzothiazolesulfenamide was prepared by a procedure similar to that of Example 1, but using a tetrapyridinoporphyrazine cobalt complex as the catalyst instead of a cobalt phthalocyanine. The yield of sulfenamide was 98.4% based on 2-mercaptobenzothiazole.

The tetrapyridinoporphyrazine was prepared from pyridine-2,3-dicarboxylic acid according to U.S. Pat. No. 3,980,582 and Chemical Abstracts, Vol. 53, (1959), 21339.

EXAMPLE 12

A series of experiments similar to those of Example 2 was carried out using isopropylamine (3.75 moles), 2-mercaptobenzothiazole (0.4 mole) and various quantities of water as shown in the table below.

| Preparation No. | % Water* | % Yield of Product Based on MBT |
|---|---|---|
| 12A | 9.1 | 89.9 |
| 12B | 4.8 | 92.7 |

-continued

| Preparation No. | % Water* | % Yield of Product Based on MBT |
| --- | --- | --- |
| 12C | 2.4 | 93.1 |
| 12D | 0.9 | 93.2 |

*% by weight based on the total weight of water plus isopropylamine.

Increase in yield with reduction in the percentage of water in the reaction medium is apparent from the results. Further reduction in the percentage of water to below 0.5% gives a small decrease in yield below the maximum, but the main effect of such further reduction is a marked increase in reaction time. High yields of N-isopropyl-2-benzothiazolesulfenamide are obtained at useful reaction rates when the amount of water in the reaction medium at the outset of the reaction is 0.5 to 5% of the weight of the mixture of water and amine.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. In a process for the production of a sulfenamide, in which a 2-mercaptobenzothiazole of the formula

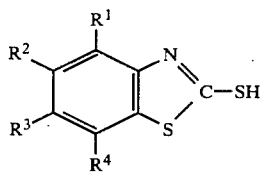

where each of $R^1$, $R^2$, $R^3$, and $R^4$ is independently hydrogen, $C_{1-6}$ alkyl, $C_{1-6}$ alkoxy, chloro- or other inert substituent, and an amine which is a primary alkylamine or cycloalkylamine, or a secondary amine having the formula

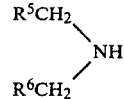

where each of $R^5$ and $R^6$ is hydrogen or an alkyl or cycloalkyl group or where $R^5$ and $R^6$ are linked such that the amine has a saturated ring structure optionally containing a heteroatom in addition to the nitrogen atom shown in the formula, are reacted with oxygen in the presence of a water-insoluble catalyst selected from metal complexes of porphyrazine and its derivatives in a reaction medium consisting essentially of water and a stoichiometric excess of the amine relative to the 2-mercaptobenzothiazole, the improvement which comprises using as the reaction medium a mixture of the amine and water in which the amount of water at the outset of the reaction is from 0.5 to 5% of the weight of the mixture.

2. A process according to claim 1 wherein the amount of amine is from 2 to 20 moles per mole of the 2-mercaptobenzothiazole.

3. A process according to claim 2 wherein the catalyst is a cobalt phthalocyanine.

4. A process according to claim 2 wherein the catalyst is a manganese phthalocyanine.

5. A process according to claim 1 wherein the catalyst is adsorbed on a water-insoluble support.

6. A process according to claim 5 wherein the support is an activated carbon.

7. A process according to claim 1 wherein each of $R^1$, $R^2$, $R^3$, and $R^4$ in the formula of the 2-mercaptobenzothiazole is hydrogen and the amine is tert-butylamine, isopropylamine, morpholine, cyclohexylamine or diethylamine.

* * * * *